United States Patent
Ye et al.

(10) Patent No.: US 10,004,472 B2
(45) Date of Patent: Jun. 26, 2018

(54) PET DETECTOR TIMING CALIBRATION

(71) Applicant: KONINKLIJKE PHILIPS N.V., Eindhoven (NL)

(72) Inventors: Jinghan Ye, Cupertino, CA (US); Xiyun Song, Cupertino, CA (US); Thomas Leroy Laurence, North Royalton, OH (US); Sharon Xiaorong Wang, Highland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/520,898

(22) PCT Filed: Oct. 15, 2015

(86) PCT No.: PCT/IB2015/057922
§ 371 (c)(1),
(2) Date: Apr. 21, 2017

(87) PCT Pub. No.: WO2016/067150
PCT Pub. Date: May 6, 2016

(65) Prior Publication Data
US 2018/0021009 A1    Jan. 25, 2018

Related U.S. Application Data

(60) Provisional application No. 62/069,011, filed on Oct. 27, 2014.

(51) Int. Cl.
*A61B 6/00* (2006.01)
*A61B 6/03* (2006.01)

(52) U.S. Cl.
CPC .............. *A61B 6/583* (2013.01); *A61B 6/037* (2013.01); *A61B 6/4266* (2013.01)

(58) Field of Classification Search
CPC ......... A61B 6/582; A61B 6/583; A61B 6/038; A61B 6/4258; A61B 6/037; A61B 6/4266
See application file for complete search history.

(56) References Cited

U.S. PATENT DOCUMENTS 7,345,281 B2    3/2008   Heukensfeldt
7,820,975 B2    10/2010  Laurence
(Continued)

FOREIGN PATENT DOCUMENTS

| JP | 2011153899 | 8/2011 |
| WO | 2006/079935 | 8/2006 |
| WO | 2014/023954 | 2/2014 |

OTHER PUBLICATIONS

Zanzonico, et al., "Routine Quality Control of Clinical Nuclear Medicine Instrumentation: A Brief Review", J Nucl Med. Jul. 2008 ; 49(7): 1114-1131.

*Primary Examiner* — David Porta
*Assistant Examiner* — Faye Boosalis

(57) ABSTRACT

A diagnostic imaging system includes a plurality of radiation detectors (20) configured to detect radiation events emanating from an imaging region. The system includes a calibration phantom (14) configured to be disposed in the imaging region spanning substantially an entire field of view and to generate radiation event pairs that define lines-of-response, wherein the calibration phantom is thin such that each LOR intersects the calibration phantom along its length, the thickness of the phantom being smaller than the length of the LORs. A calibration processor (24) receives input of the radiation detectors and calculates an incidence angle independent crystal delay $T_i$ for each detector. The calibration processor (24) constructs a first look-up table for the timing correction of each LOR and a second look-up table for the angle depth of interaction correction for each crystal by combining $T_i$ and $\eta_i$.

16 Claims, 4 Drawing Sheets

(56) References Cited

U.S. PATENT DOCUMENTS

| | | |
|---|---|---|
| 8,089,043 B2 | 1/2012 | Casey |
| 8,384,015 B2 | 2/2013 | Blevis |
| 2003/0178559 A1 | 9/2003 | Hamill |

PET DETECTOR TIMING CALIBRATION

CROSS REFERENCE TO RELATED APPLICATIONS

This application is the U.S. National Phase application under 35 U.S.C. § 371 of International Application No. PCT/IB2015/057922, filed Oct. 15, 2015, published as WO 2016/067150 on May 6, 2016, which claims the benefit of U.S. Provisional Patent Application No. 62/069,011 filed Oct. 27, 2014. These applications are hereby incorporated by reference herein.

FIELD

The present application relates generally to medical imaging. It finds particular application in calibration of a positron emission tomography (PET) detectors, and will be described with particular reference thereto. However, it is to be understood that it also finds application in other usage scenarios and is not necessarily limited to the aforementioned application.

BACKGROUND

In PET with time-of-flight (TOF) capability, reconstruction algorithms rely on precise timing calibration for each line-of-response (LOR). Current calibration methods use a positron emission point source, a cylinder source, or patient data to ascertain scintillator crystal timing. However, these sources are not advantageous for timing calibration of a PET system. Point source is small and no direct coincident event counts are available for many valid LORs. Cylindrical source is so large that along each LOR the source is distributed in a large range.

The cylinder calibration source is placed in the center of the scanner. There are some LORs that do not intersect the phantom, hence cannot be calibrated directly. In this case the actual timing difference between the scintillation crystals that define the non-intersecting LOR can only be indirectly derived. The implicit assumption behind the indirect derivation is either the delay at a crystal is independent of gamma incidence angle, or the delay at each crystal is always the same. However, larger, i.e. shallower, incidence angles may cause extra delay due to decreased average depth of interaction (DOI) of gamma photons in the scintillation crystal. The visible scintillation photons travel slower than gamma photons in the scintillation crystal which leads to timing differences attributable to the proportion of the crystal length traversed by the gamma photons. To calibrate a ring-type scanner, each LOR from the calibration source strikes the crystals at both ends the same incidence angle. Therefore it is assumed the extra delay caused by increased incidence angle is the same.

The activity in the cylindrical source is distributed in a range along the LOR, so determining the crystal timing for the LOR to the same precision as a point source requires a larger number of counts than when the activity concentrated at a single spot along the LOR. Additionally, the chance of encountering Compton scattering of the coincidence photons increases with the volume of the source. Inclusion of scattered photons in the measurement further reduces the crystal timing precision.

SUMMARY

In accordance with one aspect, A diagnostic imaging system comprises a plurality of radiation detectors configured to detect radiation events emanating from an imaging region; and a calibration phantom configured to be disposed in the imaging region spanning substantially an entire field of view and to generate radiation event pairs that define lines-of-response, wherein the calibration phantom is thin such that each LOR intersects the calibration phantom uniquely along its length, the thickness of the phantom being smaller than the length of the LORs.

In accordance with another aspect, a method for calibrating a diagnostic imaging system, comprises disposing a calibration phantom in an imaging region spanning substantially an entire field of view and to generate radiation event pairs that define lines-of-response, wherein the calibration phantom is thin such that each LOR intersects the calibration phantom uniquely along its length, the thickness of the phantom being smaller than the length of the LORs; and detecting a plurality of radiation events emanating from the imaging region.

In accordance with another aspect, a diagnostic imaging apparatus, comprises a plurality of radiation detectors disposed around an imaging region configured to detect radiation events emanating from the imaging region, the detectors having differing timing delays. The system further comprises a planar calibration phantom configured to be disposed in the imaging region the phantom including radiation sources which emit pairs of oppositely traveling radiation events which interact with the radiation detectors and define an LOR, the phantom defining a known location along each LOR. The system further comprises one or more processors configured to receive outputs from the detectors and from the known location and the relative timing of the detector outputs determining temporal correction factors for the detectors which correct for the differing timing delays among the detectors.

One advantage resides in more accurate timing calibration.

Another advantage resides in faster calibration.

Another advantage resides in reduced counts for calibration.

Another advantage resides in correcting for incidence angles in each crystal.

Still further advantages of the present invention will be appreciated to those of ordinary skill in the art upon reading and understand the following detailed description The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The present application provides a system and method to calibrate the timing in a PET system. The disadvantages can be overcome by the present application. The present application uses a sheet source or a variation of a sheet source to calibrate for TOF-PET timing. The source is a large, flat sheet such that all LORs that would intersect a subject pass through a sheet source when placed parallel to the central axis, e.g. horizontally, in the center. The sheet source can be rotated so that all LORs intersect the sheet source in at least one orientation. Using a sheet source or similar type source to serve the timing calibration results in a large LOR coverage, negligible scatter contribution, and vary narrow activity distribution along each LOR. Also, there is no need to indirectly derive LOR timings for any LOR since there are direct coincidence event counts available for each valid LOR. Because the activity is narrowly distributed along each LOR, i.e. substantially at a single point, the number of detected counts needed to achieve the same timing calibration precision is much lower.

Figure 1:
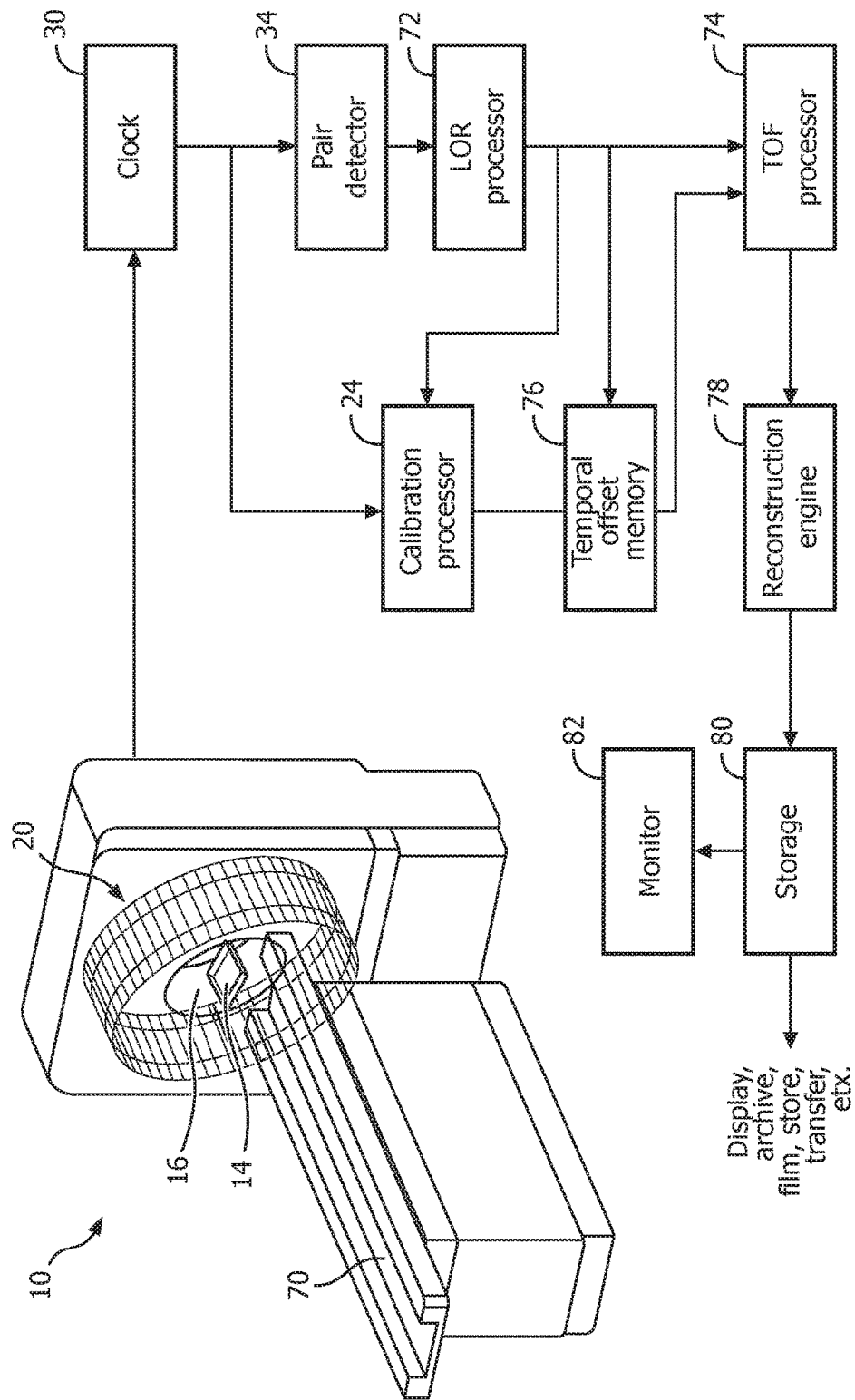
FIG. 1 illustrates a nuclear imaging system to be calibrated.

With reference to FIG. 1, an imaging system 10 is to be calibrated. The calibration technique calibrates the coincidence timing utilized in time-of-flight (TOF) measurements associated with TOF Positron Emission Tomography (TOF-PET).

A coincidence source 14 is placed within an imaging region 16 (or bore) of a PET scanner 10. The coincidence source 14 is described in further detail below. Radiation events are detected by scintillator and silicon photomultipliers (SiPM) or other detectors such as photomultiplier tubes (PMT's), or avalanche photodiodes (APDs) or the like are also contemplated of a detector array 20. A calibration processor 24 calibrates the relative timing of the detectors of the PET scanner. The calibration is described in more detail below.

Each detected gamma photon event is time stamped by a clock 30. In a digital PET system each event is typically timestamped on circuitry that supports the APD. A coincident pair detector 34 compares the timestamps of the detected events to determine pairs of events which define the end points and/or, e.g. occur within a preselected coincidences time window.

Figure 2:
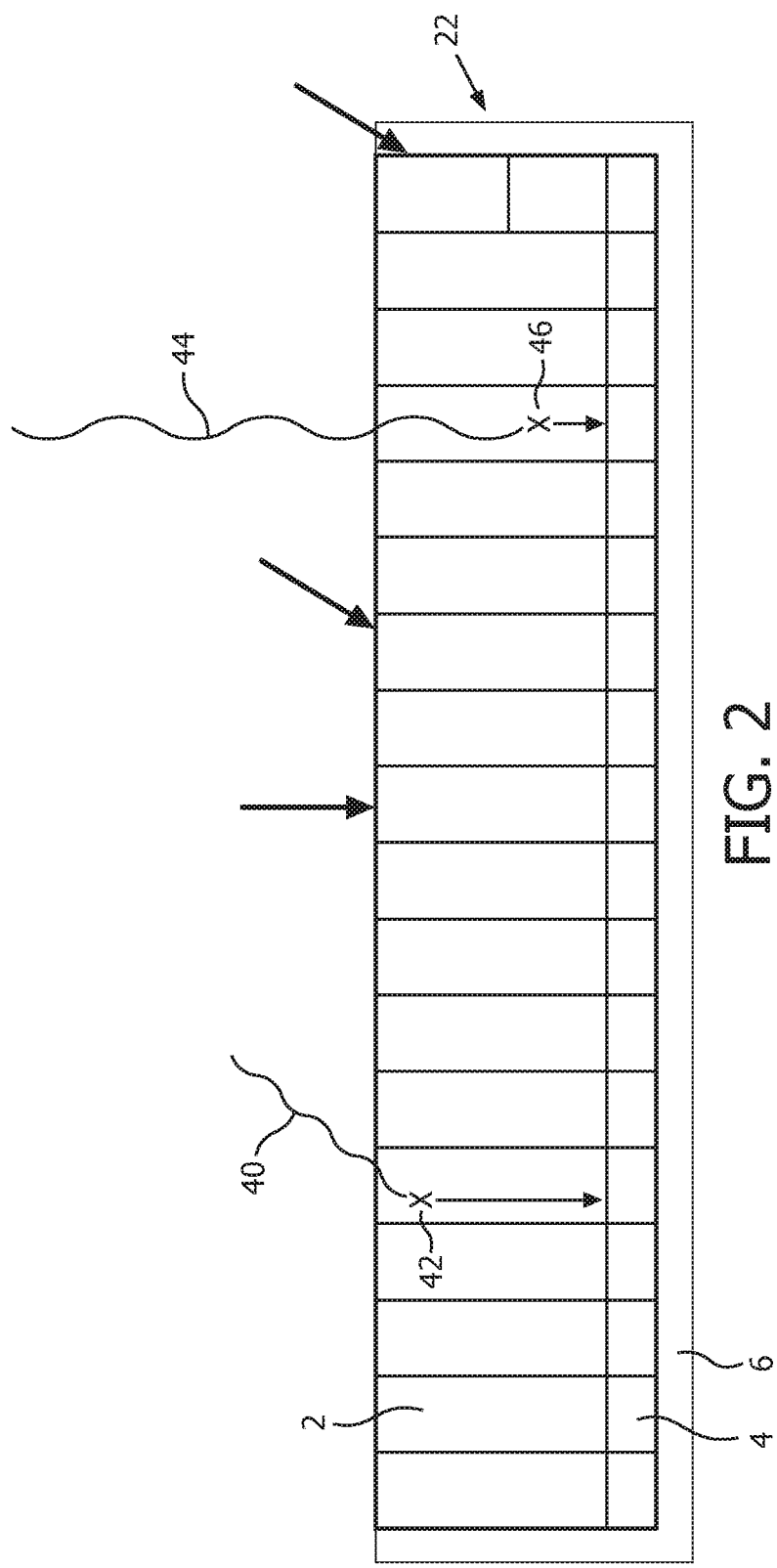
FIG. 2 depicts depths of interaction for a block detector.

With reference to FIG. 2 and continuing reference to FIG. 1, the medical imaging system 10 includes the ring of radiation detectors 20 (including crystals 2, (e.g., thousands) light detectors 4 (e.g., hundreds, thousands), and support circuitry modules 6 (e.g., tens)) arranged around the imaging region 16 to detect radiation events (e.g., gamma rays) emitted from within the imaging region 16. As depicted, the plurality of detectors 20 can be arranged in a plurality of modules 22, each of which sends digital signals indicative of at least energy and the time of each event. The scanner 10 further includes a support mechanism 70 for positioning a patient or an imaging subject in the imaging region 16. In some instances, the support mechanism 70 is linearly movable in an axial direction generally transverse to the radiation detectors 20 to facilitate acquiring three dimensional imaging data.

In preparation for imaging with the scanner 10, a suitable radiopharmaceutical is administered to the subject that will be scanned, and the subject is positioned within the imaging region 16. The radiopharmaceutical undergoes radioactive decay, which results in an emission of positrons. Each positron interacts with one or more nearby electrons and annihilates, which produces two oppositely directed (180 degree) gamma rays having energies of about 511 keV each. The two oppositely directed gamma rays may strike opposing detectors at substantially the same time, i.e., coincidentally.

The pair detector 34 identifies pairs of substantially simultaneous or coincident gamma ray detections belonging to corresponding electron-positron annihilation events. This processing can include, for example, energy windowing (e.g., discarding radiation detection events outside of a selected energy window disposed about 511 keV) and coincidence-detecting circuitry (e.g., discarding radiation detection event pairs temporally separated from each other by greater than a selected time-window).

Upon identifying an event pair, a line of response (LOR) processor 72 processes the spatial information for each pair of events to identify a spatial LOR connecting the two gamma ray detections. Since the two gamma rays emitted by a positron-electron annihilation event are oppositely spatially directed, the electron-positron annihilation event is known to have occurred somewhere on the LOR. In TOF-PET, the detectors 4 and the time stamping of the clock 30 have sufficiently high temporal resolution to detect a time-of-flight (TOF) difference between the two substantially simultaneous gamma ray detections. A TOF processor 74 analyzes the time difference between the times of each event of the coincident pair to localize the positron-electron annihilation event along the LOR. A temporal offset or correction memory 76 stores correction for temporal differences in the response time of the detectors that detected the events that define each LOR. The memory 76 is addressed by the LOR as defined by its end joints to move a temporal correction to the time-of-flight processor 74 to compensate for the relative difference in the response time of the two detectors.

A reconstruction engine 78 reconstructs the LOR into images that are stored in storage or memory 80, and can be displayed, printed, archived, filmed, processed, transferred to another device, displayed on a monitor 82, etc. A radiologist or other suitable clinician can use the raw data and/or reconstructed image to control the TOF-PET scanner 10, diagnose the subject, etc.

It is to be appreciated that the processing described above as well as other processing can be performed by one or more processing components. Thus, the processing described herein can be processed by a single processing component, individual processing components, different combinations of processing components, and/or a combination thereof.

To calibrate the nuclear scanner 10 particularly to determine the temporal corrections to store in the temporal correction memory, the phantom is placed in the scanner 10 and is conveniently oriented horizontally. The sheet source 14 is placed at approximately the center of the scanner and approximately horizontal. A number of coincidence events are recorded by the scanner 12 in a list mode acquisition. Each coincidence event includes which two crystals detect concurrent events and the timing difference between the two crystals. In another embodiment, an event time histogram for each LOR is used when a non-planar source is used, such that an LOR may intercept the phantom two or more times, there will be more than one peak along the LOR histogram.

Figure 3:
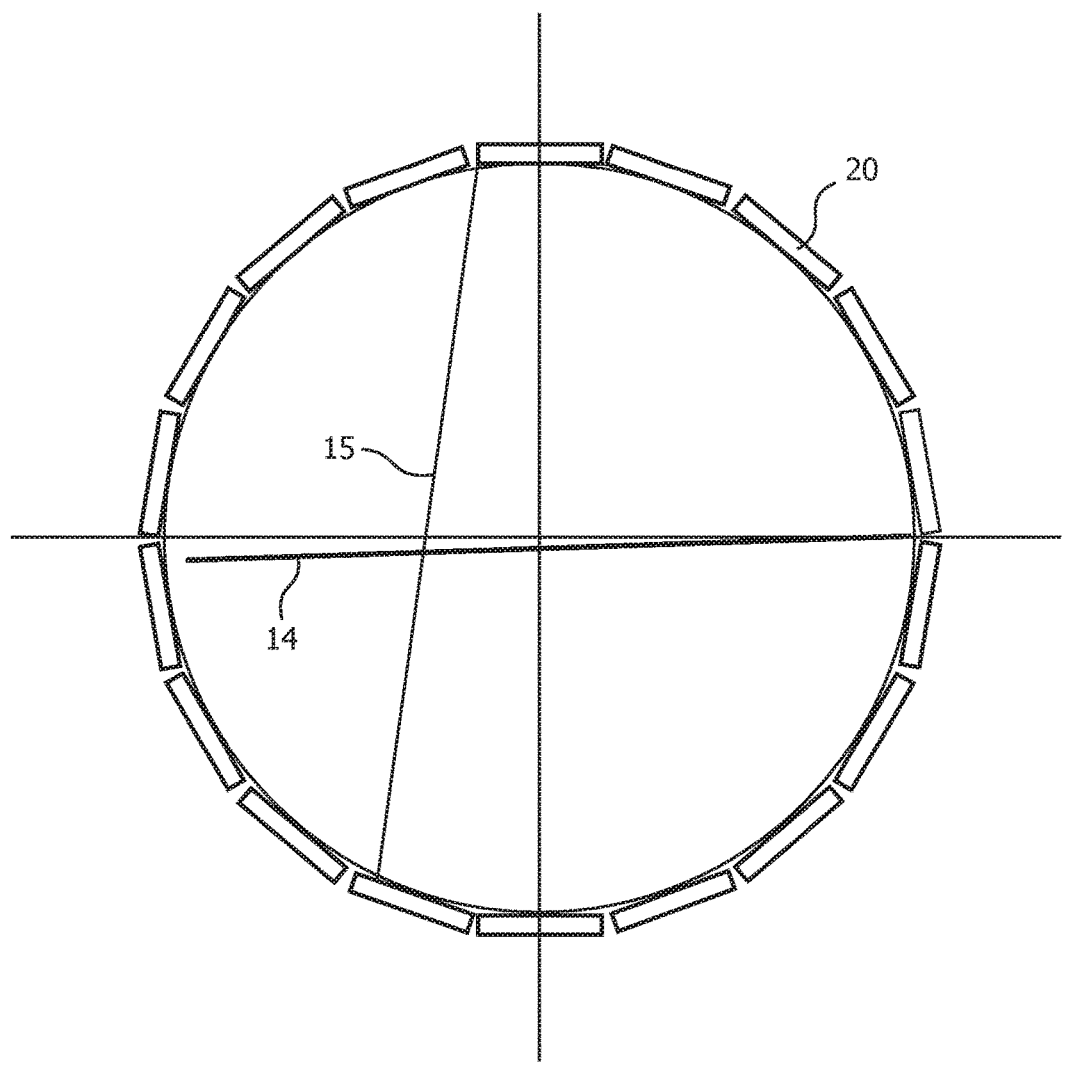
FIG. 3 illustrates orientations of a sheet source.
Figure 4:
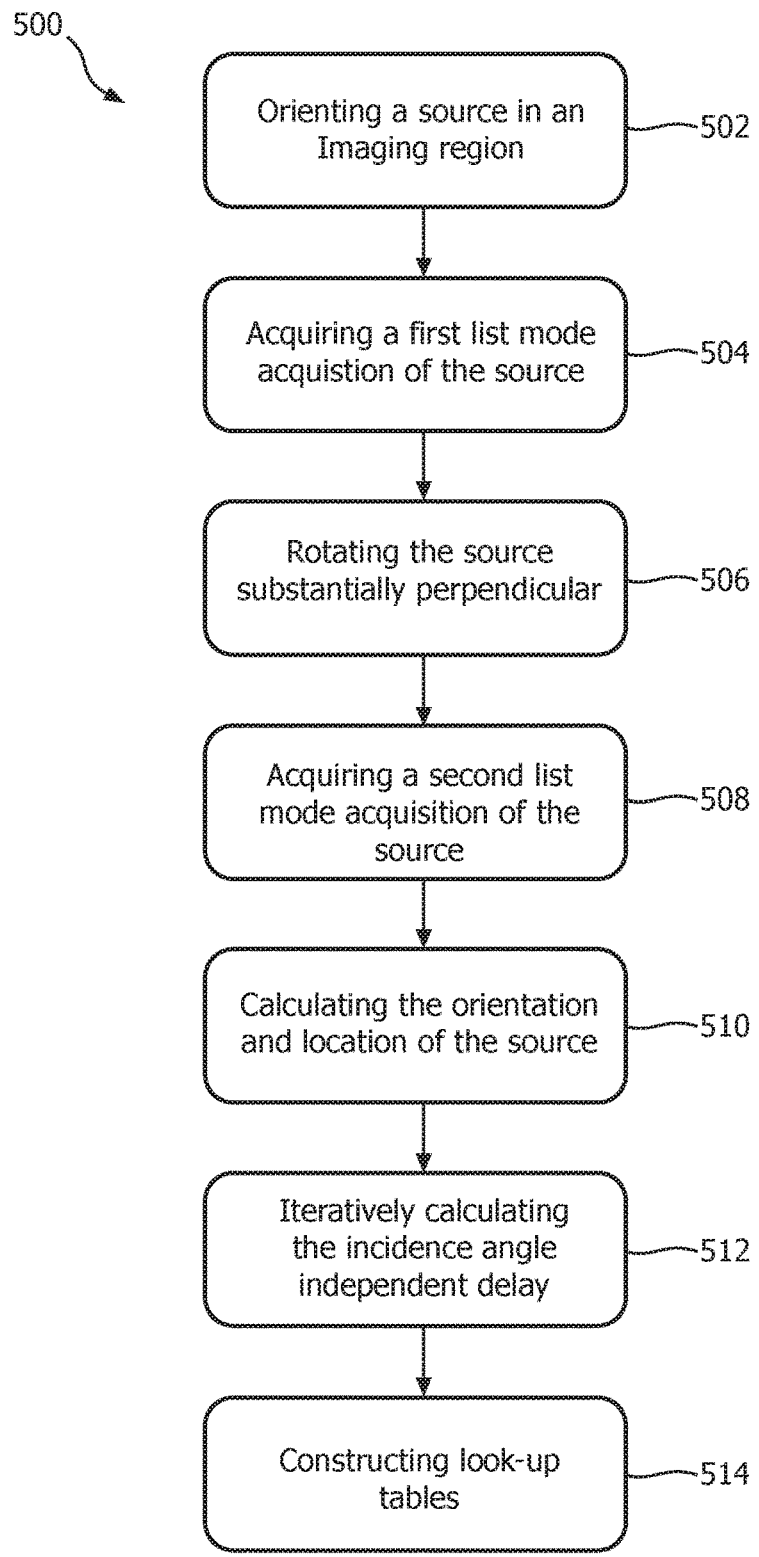
FIG. 4 depicts a method for calibrating an imaging system.

With reference to FIG. 3, in one embodiment, after the present number of events is recorded, the sheet source 14 is rotated to another orientation 15, e.g. generally vertically, and a subsequent list mode acquisition is performed. In one embodiment, at least two nearly perpendicular orientations are used to make sure that all LORs pass through the sheet source 14 at least in one orientation. In one embodiment, a flat sheet source is used, although other shapes of the source 14 are also contemplated.

Other embodiments contemplate different shaped sources such as a thin cylindrical shell and a spinning line source. This type of phantom uses a single acquisition if the radius of the shell is larger than the transverse FOV. In this embodiment, there are two interception points of the phantom with each LOR.

In another embodiment, a shell shape composed of three or four planar sources is used. In this embodiment, a subsequent acquisition with the phantom rotated by about 60 degrees captures the LORs that are not intercepting the phantom to intercept the phantom.

In one embodiment, the source 14 has a relatively large area and a relatively small volume. The large area of the source 14 covers the entire or substantially the entire field of view (FOV) which results in more LORs through the source in a single measurement. The small volume of the source, particularly a thin layer, restricts the activity within a narrow range along each LOR so that the counts needed are reduced compared to a larger volume source spanning a wide range. For example, a sheet source 14 that is about 70 cm by 70 cm by 1.5 mm thick is an example of a large area and a small volume. The thin volume causes less for scattering of gamma photons. In another embodiment, the sheet source 14 is constructed from an array of point sources. In another embodiment, the source is thin relative to the width of a scintillation crystal.

The calibration processor 24 determines the position and orientation of the source 14 either from a non-time-of-flight (non-TOF) sinogram of the sheet source 14 or by other means. In one embodiment, a phantom holder is used such that the location and orientation is already known. After the location and orientation of the sheet source is determined, the calibration processor 24 determines the point where the event LOR intercepts with the plane of the source 14. The intercept point is where the coincidence gamma photons originate. The calibration processor 24 calculates the time needed for each gamma photon to reach a detector crystal. The expected time difference $E_{ij}$ for $LOR_{ij}$ is determined, where i and j are the crystal indices for the LOR. If the counts for each LOR are high enough, the difference between $E_{ij}$ and $\overline{M_{ij}}$ is the timing calibration for $LOR_{ij}$, where $\overline{M_{ij}}$ is the mean measured time difference from all the events belonging to the LOR.

Typically a modern 3D PET scanner may have about a few hundred million valid LORs, with each LOR having about several thousand counts to reach a timing precision level of a few percent resulting in about 1 trillion counts. If a volumetric source is used, the required counts are a magnitude higher due to a wider distribution of the source in an LOR. Therefore, it is time consuming to acquire enough counts for all LORs to reach the desired timing precision. However, if the timing of a detector crystal does not vary with the gamma incidence angle, then the calibration processor 24 calculates the crystal delay in an iterative process that minimizes the least squared error to solve the count deficiency.

For a measured coincidence event belonging to $LOR_{ij}$, where i and j are crystal indices, the expected time difference without crystal delay is $E_{ij}$. To factor for crystal delays of $\tau_i$ and $\tau_j$ at crystals i and j respectively, the calibration processor 24 calculates the expected measured time difference for the event using $(E_{ij}-\tau_i+\tau_j)$. The sum of the squared error for all events is $$Q = \sum_{events} (M_{ij} - E_{ij} + \tau_i - \tau_j)^2 \qquad (1)$$

The partial derivative of Q with respect to $\tau_i$, is $$\frac{\partial Q}{\partial \tau_i} = \sum_{events_i} (M_{ij} - E_{ij} + \tau_i - \tau_j) = 0 \qquad (2)$$

where the summation includes events linked to crystal i. Solving for a specific $LOR_{ij}$, results in $$\frac{dQ_j}{d\tau_i} = \sum_{events \in (i,j)} (M_{ij} - E_{ij} + \tau_i - \tau_j) = n_{ij}\overline{M_{ij}} - n_{ij}E_{ij} + n_{ij}\tau_i - n_{ij}\tau_j \qquad (3)$$

where $n_{ij}$ is the number of events in $LOR_{ij}$. Using this equation, the least squared error for all events is $$\frac{\partial Q}{\partial \tau_i} = \qquad (4)$$

$$\sum_j n_{ij}(\overline{M_{ij}} - E_{ij} + \tau_i - \tau_j) = \sum_j n_{ij}(\overline{M_{ij}} - E_{ij} - \tau_j) + \tau_i \sum_j n_{ij} = 0.$$

The equation is solved for crystal delay of crystal i, $\tau_i$ to get $$\tau_i = \frac{\sum_j n_{ij}(E_{ij} - \overline{M_{ij}} + \tau_j)}{\sum_j n_{ij}}. \qquad (5)$$

Exact knowledge of $\tau_i$ cannot be determined analytically. However, the calibration processor 24 calculates an iterative process for $\tau_i$, as $$\tau_i^{(n+1)} = (1-\alpha)\tau_i^{(n)} + \alpha \frac{\sum_j n_{ij}(E_{ij} - \overline{M_{ij}} + \tau_j^{(n)})}{\sum_j n_{ij}} \qquad (6)$$

where $\alpha$ is a dumping factor in (0, 1] to control the convergence rate. However, the crystal delay at each crystal is not constant; it is dependent on the gamma incidence angle. The expected measured time difference for an event becomes $(E_{ij}-\tau_i-\eta_i(\phi_{ij})+\tau_j+\eta_j(\phi_{ji}))$, where $\phi_{ij}$ is the gamma incidence angle to crystal i for $LOR_{ij}$, and $\eta_i$ is the incidence angle dependent timing adjustment for crystal i, and $\eta_i(0)=0$. The incidence angle dependent factor $\eta_i$ is independent on the crystal delay $\tau_i$ and does not vary from system to system for the same model of system. The incidence angle dependent factor is determined and saved using bench top measurements or Monte Carlo simulations. In one embodiment, symmetry is used so that the number of $\eta_i$ stored is reduced.

Knowing $\eta_i$ for each crystal, the calibration processor 24 adjusts the expected time difference for each event belonging to a $LOR_{ij}$ is to be $E'_{ij}=(E_{ij}-\eta_i(\phi_{ij})+\eta_j(\phi_{ji}))$. Substituting $E_{ij}$ by $E'_{ij}$ into Eqn. (6) finds the incidence angle independent delay $\tau_i$. During a list mode TOF reconstruction, $\tau_i$ and $\eta_i$ are combined to provide the timing correction factor for crystal i.

The number of LORs associated with crystal i is large when using the sheet source 14. For example, greater than one fourth of the crystals may establish valid LORs with a single crystal. The total number of required counts is reduced by almost three magnitudes or in the order of a billion total coincidence counts from the acquisition of the sheet source. If 6 orientations are used for the acquisition, then each needs about 160 million counts. About half of the counts are from LORs that have a too shallow incidence angle through the sheet source, which means an acquisition of about 300 million counts per orientation for 6 orientations is sufficient. The calibration processor 24 constructs lookup tables for the calculated timing correction for each LOR. The calibration processor 24 constructs a lookup table for the calculated incidence angle correction for each crystal.

It is appreciated that the above derivation and methodology are applicable to other shaped sources. For example, a uniform cylinder source can be used, however the required total counts is increased due to the larger volume. A cylinder source can be used; however it would require multiple acquisitions with the cylinder source moved around. Another example is using a point source, where a point source is a smaller version of a cylinder source.

Another example variation is combining two sheet sources to form a cross structure. In another embodiment, three sheet sources form a triangle which results in either one or two LOR-to-source-plane interception points. From measured timing difference in each event, the calibration processor 24 can determine from which sheet the event is likely initiated. Using such kind of source reduces the number of acquisitions per timing calibration. In another embodiment, a cylinder or point source is used in combination with a sheet source.

With reference to FIG. 5, a method 500 for calibrating an imaging system is depicted. At a step 502, a sheet source is oriented in the imaging region of the imaging system. At a step 504, a first list mode acquisition of the sheet source is performed to receive LOR data for crystal pairs. At a step 506, the sheet source is rotated substantially perpendicular from the first orientation. At a step 508, a second list mode acquisition of the rotated sheet source is performed. The rotation and second list mode acquisition steps ensure that all LORs travel through the sheet source at least once either during the first list mode acquisition, the second list mode acquisition or both. At a step 510, the orientation and location of the source are first calculated. This calculation is used to determine an intercept point of a gamma photon on the sheet source. At a step 512, the incidence angle independent delay is calculated using the derivation described above. At a step 514, look-up tables are constructed for the timing correction for each LOR and the angle depth-of-interaction correction for each crystal in the detector.

The gamma photon travels through the subject, the air around the subject, and the scintillation crystal substantially at the speed of light in a vacuum. When the gamma photon interacts with the scintillator it is converted into light, i.e. a scintillation. The light travels through the crystal at a speed significantly slower. Thus, the time between the annihilation event and the output from the detector varies with the depth of interaction of the gamma photon with the crystal. The point at which the gamma photon interacts with the crystal is probabilistic. During calibration, a curve of the depth of interaction vs. number of interactions is a Gaussian. The calibration can determine the timing offset or correction for each detector or pair of detectors to align the peaks of the Gaussian.

In one embodiment, a timing correction or offset for each passable LOR is determined. That is a single timing correction for the pair of detectors that define each LOR.

In another embodiment, a timing correction or offset is determined for each detector based on gamma photons that strike the crystal generally perpendicular to its face. With reference to FIG. 2, the gamma photons 40 that strike the crystal at an obtuse angle are constrained by geometry to interact and scintillate 42 with an upper (entrance face) end of the crystal. That is, the depth of interaction Gaussian will peak near the entrance face. Gamma photons 44 which enter substantially perpendicular to the face can interact and scintillate 46 any depth in the crystal. The depth of interaction of gamma photons entering at angles in between, are contained to greater or lesser degrees. A second, geometric correction factor based on the angle between a LOR on the detector is determined. As can be seen in FIG. 3, the detector modules are symmetric, as only a limited number of geometric correction factors can be stored. During imaging, when an LOR is determined, the scintillators that define its end points and the angle between the crystal face and the LOR are determined. The timing corrections of the end point crystals and the geometric timing corrections based on the incidence angles are relieved from the memory 76 and provided to the TOF processor 74.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), a FPGA, and the like; a controller includes any device or system controlling another device or system, and typically includes at least one processor; a user input device includes any device, such as a mouse or keyboard, allowing a technician of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A diagnostic imaging system, comprising:
   a plurality of radiation detectors configured to detect radiation events emanating from an imaging region;
   a calibration phantom configured to be disposed in the imaging region spanning substantially a length and width of a field of view and to generate radiation event pairs that define lines-of-response, wherein the calibration phantom includes a sheet source such that each LOR intersects the calibration phantom; and
   a calibration processor configured to receive input from the radiation detectors and calculate an incidence angle dependent crystal delay $\tau_i$, for each detector.

2. The system according to claim 1, wherein the calibration phantom is configured to be disposed in the imaging region at offset orientations during calibration.

3. The system according to claim 1, wherein the calibration processor is configured to determine the orientation and location of the calibration phantom in the field of view and at least one intersection of the phantom and each LOR.

4. The system according to claim 3, wherein the calibration processor is further configured to calculate the difference between an actual detection time and an expected detection time.

5. The system according to claim 4, wherein the calibration processor further configured to iteratively calculate a crystal delay using $$\tau_i^{(n+1)} = (1-\alpha)\tau_i^{(n)} + \alpha \frac{\sum_j n_{ij}(E_{ij} - \overline{M_{ij}} + \tau_j^{(n)})}{\sum_j n_{ij}},$$

wherein i and j are crystal indices, α is a dumping factor, E is the expected time difference, M is the mean measured time difference, n is the number of events.

6. The system according to claim 4, wherein the calibration processor is further configured to substitute E with E' into the iterative calculation, such that $E'_{ij}=(E_{ij}-\eta_i(\phi_{ij})+\eta_j(\phi_{ji}))$ wherein $\phi_{ij}$ is the gamma incidence angle to crystal i and $\eta_i$ is the incidence angle dependent timing adjustment for crystal i.

7. The system according to claim 1, wherein the calibration processor is further configured to construct a first look-up table for the timing correction of each LOR and a second look-up table for the angle depth of interaction correction for each crystal by combining $\tau_i$ and $\eta_i$.

8. A method for calibrating a diagnostic imaging system, comprising:
   disposing a calibration phantom in an imaging region spanning substantially an entire field of view and to generate radiation event pairs that define lines-of-response (LOR), wherein the calibration phantom spans a length and width of a field of view such that each LOR intersects the calibration phantom;
   detecting a plurality of radiation events emanating from the imaging region;
   receiving input of the radiation detectors;
   determining a location of the phantom along each LOR; and
   calculating an incidence angle independent crystal delay $\tau_i$, based on the received input.

9. The method according to claim 8, comprising:
   acquiring a first list mode acquisition wherein the calibration phantom is sized and oriented to maximize the number of LORs going through it during the first list mode acquisition.

10. The method according to claim 8, comprising:
    disposing the calibration phantom in the imaging region at substantially 90 degrees offset orientations during calibration, wherein the phantom is planar.

11. The method according to claim 8, comprising:
    determining the orientation and location of the calibration phantom in the field of view and at least one intersection of the phantom and each LOR.

12. The method according to claim 8, comprising:
    calculating the difference between an actual detection time and an expected detection time.

13. The method according to claim 8, comprising:
    iteratively calculating a crystal delay using $$\tau_i^{(n+1)} = (1-\alpha)\tau_i^{(n)} + \alpha \frac{\sum_j n_{ij}(E_{ij} - \overline{M_{ij}} + \tau_j^{(n)})}{\sum_j n_{ij}},$$

wherein i and j are crystal indices, α is a dumping factor, E is the expected time difference, M is the mean measured time difference, n is the number of events.

14. The method according to 13, comprising:
    substituting E with E' into the iterative calculation, such that $E'_{ij}=(E_{ij}-\eta_i(\phi_{ij})+\eta_j(\phi_{ji}))$ wherein $\phi_{ij}$ is the gamma incidence angle to crystal i and $\eta_i$ is the incidence angle dependent timing adjustment for crystal i.

15. The method according to claim 8, comprising:
    constructing a first look-up table for the timing correction of each LOR by combining $\tau_i$ and $\eta_i$; and
    constructing a second look-up table for the angle depth of interaction correction for each crystal.

16. A diagnostic imaging system comprising:
    a plurality of radiation detectors disposed around an imaging region configured to detect radiation events emanating from the imaging region, the detectors having differing timing delays;
    a calibration phantom configured to be disposed in the imaging region the phantom including radiation sources which emit pairs of oppositely traveling radiation events which interact with the radiation detectors and define an LOR, the phantom being at a known location along each LOR; and
    one or more processors configured to:
       receive outputs from the detectors and, from the known location and a relative time of the detector outputs to determine temporal correction factors for the detectors which correct for the differing timing delays among the detectors,
       construct a first look-up table for the temporal correction factors of each LOR and a second look-up table for the angle of incidence dependent depth of interaction correction for each crystal using an iterative calculation of an incidence angle independent crystal delay $\tau_i$, and
       reconstruct images from the LORs with localization along each LOR based on the relative time of the detector output using the look-up tables to correct the relative times of the detector outputs.

* * * * *